(12) United States Patent
Halm

(10) Patent No.: US 7,677,888 B1
(45) Date of Patent: Mar. 16, 2010

(54) COMBINATION PLACEMENT TOOL AND LIGHT

(76) Inventor: Gary V. Halm, 821 N. Fielder, Arlington, TX (US) 76012

( * ) Notice: Subject to any disclaimer, the term of this patent is extended or adjusted under 35 U.S.C. 154(b) by 0 days.

(21) Appl. No.: 11/480,293

(22) Filed: Jun. 30, 2006

Related U.S. Application Data

(60) Provisional application No. 60/696,604, filed on Jul. 5, 2005.

(51) Int. Cl.
*A61C 1/00* (2006.01)
*A61C 17/06* (2006.01)

(52) U.S. Cl. .......................... 433/29; 433/91
(58) Field of Classification Search .................. 433/29, 433/91, 163; 294/64.1; 222/566, 570; 604/275
See application file for complete search history.

(56) References Cited

U.S. PATENT DOCUMENTS 4,822,278 A * 4/1989 Oliva et al. ................ 433/91
5,882,194 A * 3/1999 Davis et al. ................ 433/29
6,350,123 B1 * 2/2002 Rizoiu et al. ............... 433/80
7,029,277 B2 * 4/2006 Gofman et al. ............. 433/29
7,066,732 B2 * 6/2006 Cao ........................... 433/29
7,083,313 B2 * 8/2006 Smith ........................ 362/555

* cited by examiner

*Primary Examiner*—Cris L Rodriguez
*Assistant Examiner*—Heidi M Eide
(74) *Attorney, Agent, or Firm*—Law Office of William R. Gustavson, PC

(57) ABSTRACT

A combination placement tool and light device (10, 50) is disclosed which allows the dentist or surgeon to hold a dental appliance with a vacuum supplied to a flexible skirt (18, 90), position the dental appliance, and then tack the dental appliance in place with a light source (28, 60, 62) using light activated adhesive. The device (10, 50) can also be used to provide a full cure. The device (10, 50) can also have a source of drying air to aid the procedure. The device (50) can be used with a disposable molded acrylic collimator (76).

18 Claims, 4 Drawing Sheets

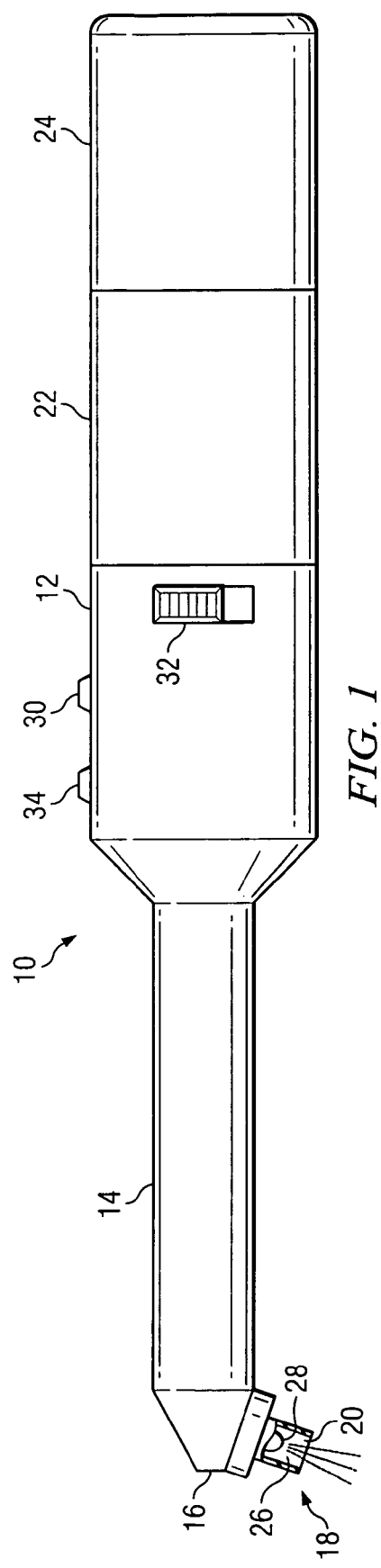
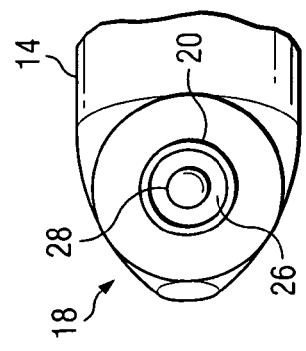

COMBINATION PLACEMENT TOOL AND LIGHT

CROSS REFERENCE TO RELATED APPLICATION

This application claims priority from Provisional Patent Application Ser. No. 60/696,604 filed Jul. 5, 2005.

TECHNICAL FIELD

This invention relates to dental and surgical bonding procedures, and in particular to assisting those procedures with an improved device.

BACKGROUND OF THE INVENTION

A dentist or surgeon will often position a dental appliance in the mouth and tack it in place with a light sensitive adhesive to evaluate the placement. Once the desired placement is achieved, the adhesive is then light cured to permanently secure the dental appliance. However, it is difficult to assure proper positioning of the appliance and to assure the position is maintained while the adhesive is activated. A need exists for a device and technique to facilitate this operation.

SUMMARY OF THE INVENTION

In accordance with one aspect of the present invention, a combination device is provided which has a source of vacuum to hold a dental appliance for initial placement and a light source to activate an adhesive to fix the appliance in the chosen position. The light source can tack the dental appliance in position and then cure the light activated adhesive in a final step.

In accordance with another aspect of the present invention, the device has a handle and an extension with a flexible skirt mounted on the end of the extension. A vacuum is created within the interior of the skirt to grasp a dental appliance. A tack light source is mounted on the extension and lies within the interior of the skirt to permit the dental appliance to be tacked in a desired location using light activated adhesive.

In accordance with another aspect of the present invention, the flexible skirt is disposable. A pump can be mounted on the handle of the device to generate the vacuum. A curing light source can also be mounted on the device to fully cure the adhesive. Air under pressure can also be supplied from the device for drying.

BRIEF DESCRIPTION OF THE DRAWINGS

For a more complete understanding of the present invention and the advantages thereof, reference is now made to the following Detailed Description, taken in conjunction with the accompanying Drawings, in which:

FIG. 1 is a schematic view of a first embodiment of the present invention;

FIG. 2 is an end view of the flexible, disposable skirt;

DETAILED DESCRIPTION

Figure 3:
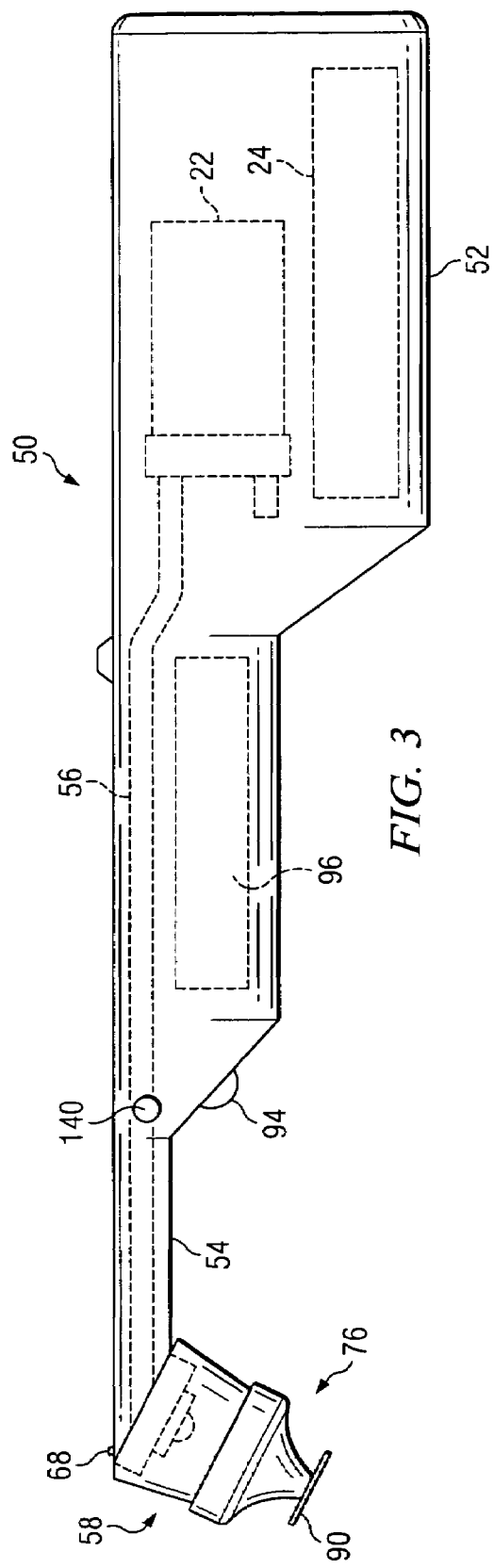
FIG. 3 is a schematic side view of a second embodiment of the present invention.
Figure 7:
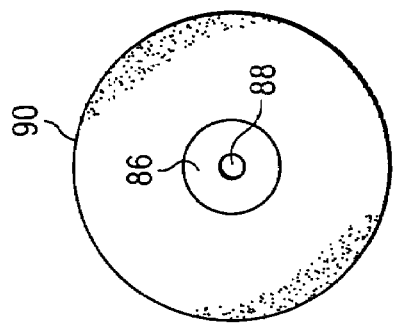
FIG. 7 is an end view of the collimator.

With reference now to the drawings, a combination placement tool and light device 10 forming a first embodiment of the present invention will be described. The device 10 allows a dental appliance to be manipulated in position while being held by vacuum at an end of the device 10 and allows the dental appliance to be tacked in position by exposure to a light source on the device 10. The device can also perform a full cure to permanently attach the dental appliance using light activated adhesive.

The device 10 includes a handle 12 for grasping by an operator and an extension 14 extending from one end of the handle 12. A removable and replaceable flexible vacuum skirt 18 is mounted near the end 16 of the extension which can maintain a vacuum therein to hold a dental appliance for positioning in the mouth. The flexible skirt 18 can touch a dental appliance so that the skirt 18 is deformed over a portion of the dental appliance to create a seal. The vacuum then holds the dental appliance on the skirt 18 to allow the dental appliance to be moved with device 10 to a desired location. The skirt 18 can be mounted to the extension 14 with adhesive, a mechanical coupling, magnetic coupling or any other suitable fastening system. Skirt 18 is preferably disposable so that a new skirt can be mounted on the device 10 for each patient to maintain sterility. The skirt 18 is mounted so that one end thereof is closed off by the extension 14, while the other end 20 is open. The open end 20 may have dimensions of 2 to 3 square mm, for example.

A vacuum pump 22 is preferably mounted on the end of the handle 12 opposite extension 14. A power source, such as batteries 24, can be mounted in the handle 12 to power the pump 22. Alternatively, a battery pack, containing batteries 24 could be mounted on the end of the handle 12 between the handle 12 and pump 22 as shown in FIG. 1. The vacuum pump generates a vacuum that is conveyed within a passage (not shown) in the handle 12 and extension 14 to the interior cavity 26 of the skirt 18.

A light source 28, preferably an LED of wavelength about 465 nm, is mounted in the extension 14 so that it shines into the interior cavity 26 of the skirt 18 in a tight beam. For example, the light source may have a narrow 1 to 2 degree beam. Preferably, the light source 28 is concentric with the skirt 18 as seen in FIGS. 1 and 2. Batteries 24 also power the light source 28.

The device 10 can be used to grasp a dental appliance with vacuum by placing the open end 20 of the skirt 18 on the appliance. The device 10 can then be manipulated to position the dental appliance in the desired location in the mouth. The light source 28 can then be used to tack the appliance in place by activating a suitable adhesive on the dental appliance. Outside areas can then be trimmed. When the final positioning is achieved, device 10 can be used to cure the adhesive to permanently bond the dental appliance in place.

A vacuum switch 30 can be mounted on the handle to start the pump 22 to generate the vacuum to hold the dental appliance. A slide switch 32 can be mounted on the handle to activate the light source 28 to tack the dental appliance in place. The vacuum switch 30 can be designed so that slide switch 32 can't be switched on when the vacuum switch 30 is on. The slide switch 32 can be a simple on-off switch, or can include a timer that causes the light source 28 to be active for a set period of time. A cure switch 34 can be mounted on the handle 12 to cure the adhesive to permanently bond the dental appliance.

The device 10 can also provide a drying air output for use in treatment procedures. Pump 22 could provide the air by taping into the discharge from the pump 22 and supplying it through another passage in the handle 12 and extension 14 opening at end 16. Alternatively, a valving structure could be provided with the pump 22 to supply a vacuum or air under pressure selectively in a single passage depending on need. Of course, an exterior source of air under pressure could be utilized and a line simply extended to the device 10 to supply the air.

A combination placement tool and light device 50 illustrated in FIGS. 3-13 forms a second embodiment of the present invention. Numerous elements of device 50 are identical to elements in device 10 and are labeled with the same references numerals in the figures.

Device 50 also includes a handle 52 and an extension 54. A tube 56 within the extension 54 carries the vacuum from vacuum pump 22 to the head 58 at the end of the extension. Tube 56 passes through the extension 54 and forms a hollow heat sink. Preferably, both tube 56 and head 58 are copper.

Head 58 mounts a light source 60 centrally thereon. Preferably, light source 60 is a blue LED having a wavelength of about 465 nm. The head includes a spherical mirror reflector 180. Also mounted in the head 58, and surrounding light source 60, are four light sources 62. Light sources 62 are preferably ultra violet LED light sources having a wavelength of about 400 nm. Both the 465 nm and 400 nm light sources can be used for tacking or full curing, depending on the presence or absence of the removable collimator 76 described hereinafter. Both wavelengths are used to accommodate a wide range of polymerization activators.

Figure 5:
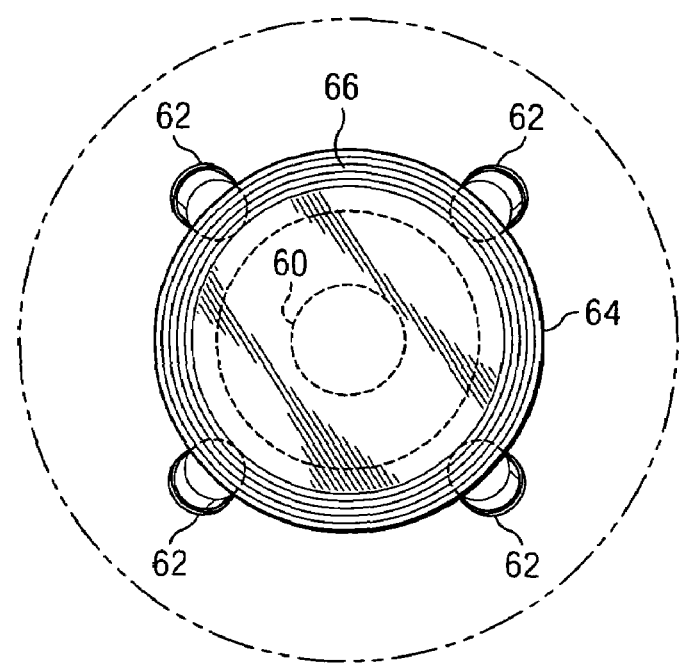
FIG. 5 is an end view of the lens.
Figure 8:
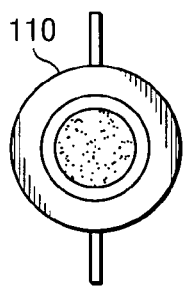
FIG. 8 is an end view of a magnetic coil.
Figure 9:
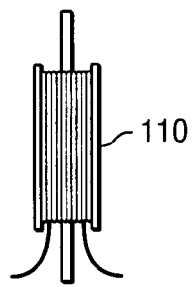
FIG. 9 is a side view of the magnetic coil.

A complex lens 64, best seen in FIG. 5, is mounted in front of the light sources 60 and 62. The complex lens is a convex lens over most of its area, but has Fresnel lens areas 66 positioned in front of the UV light sources 62, as seen in FIG. 5. Preferably, the lens 64 is about 10 mm in diameter.

Extension 54 also has an air discharge hole 68 for drying a selected area.

A bezel 70 on head 58 mounting the lens 64 also has a number of vacuum ports 72 distributed about its periphery connected to tube 56 to convey vacuum. Bezel 70 also mounts an O-ring 74 about its outer circumference.

Figure 6:
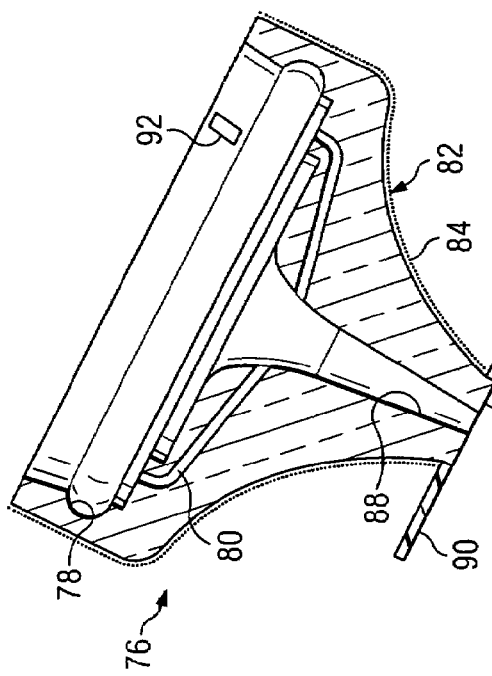
FIG. 6 is a cross sectional view of a collimator.
Figure 4:
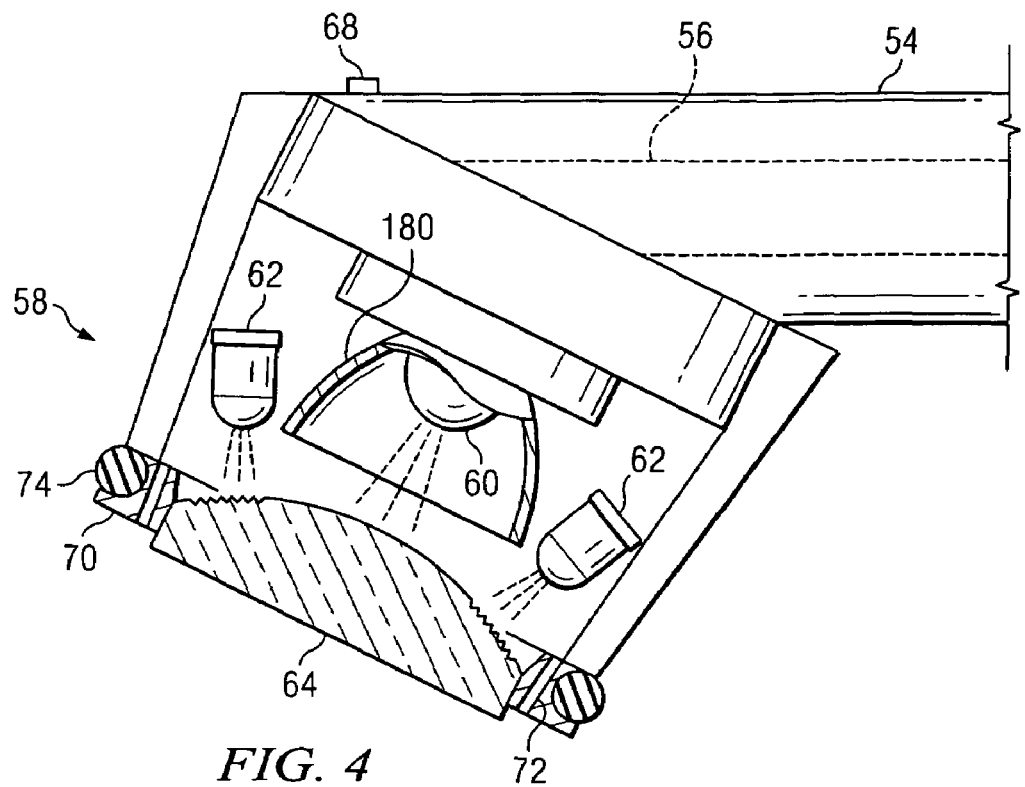
FIG. 4 is a detail view of the embodiment of FIG. 3.

A disposable molded optical acrylic collimator 76 can be mounted on the head 58 at bezel 70. For example, the collimator 76 can snap on the head 58. As seen in FIG. 6, the collimator 76 has an O-ring seat 78 to contact the O-ring 74 and form a seal. Vacuum ports 80 in the collimator 76 are aligned with the vacuum ports 72 in the bezel 70. The exterior surface 82 of the collimator 76 preferably has a hyperbolic funnel shape and has an opaque coating 84 to prevent light energy from light sources 60 and 62 from escaping from the collimator 76 other than through the planar end 86 of the collimator 76. A hyperbolic hollow tunnel 88 is formed through the center of the collimator 76 for conveying vacuum to the end 86. The tunnel 88 is connected to the ports 80 so that vacuum can be supplied through tube 56, ports 72, ports 80 and finally to tunnel 88. The O-ring seal 74 prevents loss of vacuum exterior the device 50. A thin rubber or other high compliance polymer disc 90 is mounted on the collimator 76 around end 86 to contact and conform to the dental appliance to be held to create an air tight seal with the dental appliance, allowing the vacuum from tunnel 88 to create the holding force. The disc can be 8 mm in diameter, for example. A strain gage pressure sensitive switch 92 is mounted on the bezel 70 to sense the presence of the collimator 76 to assist control functions as will be described hereinafter. The light sources 60 and 62 are connected together electrically. In other words, either both light sources 60 and 62 are on, or they are both off. By using the collimator 76, the intensity and foot print of the light sources 60 and 62 falling on the dental appliance will only be sufficient to tack the appliance in place. To fully cure the appliance, the collimator will be removed, allowing the full light intensity of sources 60 and 62 to fall on the appliance.

A main switch 94 is mounted on device 50 and cooperates with logic circuits 96 mounted within the device 50 for controlling operation of the device 50. When a collimator 76 is not mounted on the device 50, switch 92 is not activated and the main switch 94 can be turned on to power the light sources 60 and 62 to cure, which are typically powered for a set time interval, for example 10 seconds. No vacuum operation is possible without the collimator 76 installed.

When the collimator 76 is mounted to device 50, the pressure sensitive switch 92 is closed and the logic circuits 96 control operation as follows. When main switch 94 is turned on, the vacuum pump or source of vacuum is activated to generate an appropriate vacuum in tunnel 88 to hold the dental appliance. In addition, when pressure sensitive switch 92 is closed, the logic circuits require two different cure states A and B to be selected. Mounted on device 50 are two momentary switches 140 and 142 (only switch 140 is shown in FIG. 1 as the switch 142 is at the same position on the opposite side of the device). Pressing switch 140 selects cure state A. Pressing switch 142 selects cure state B. Both cure states A and B must be selected that is both switches 140 and 142 must be pressed simultaneously for light sources 60 and 62 to be activated. This is to prevent premature cure, before the dental appliance is in place. If neither cure state is selected, or only state A or B is selected, turning on main switch 94 simply turns on the vacuum. When both cure states A and B are selected, a cure time interval circuit in logic circuits 96 activate the light sources and vacuum for a set interval, for example 5 seconds, which is not repeated unless the main switch 94 is turned off and back on again. The logic circuits 96 can create an automatic shut off condition after this set interval so that the operator can simply turn main switch 94 back on again to repeat an operation. The light intensity from light sources 60 and 62 exiting end 86 of the collimator 76 is just sufficient to tack the dental appliance in place, but not perform a full cure. Device 50 can also require switches 140 and 142 to be closed simultaneously to operate light sources 60 and 62 when the collimator 76 is not used as well.

The device 50 preferably can be manufactured in three different styles. As described above, the device 50 has a self contained vacuum source and a curing function and can be described as freedom air tweezers. This device is hand held and cordless and forms a vacuum placement wand with spot curing snap-on attachment and a wide bore, say 10 to 12 mm, curing window. Wavelength peaks are at 400 and 465 nm, enabling polymerization activation for all current activation capabilities.

Device 50 could also be constructed without curing capability, being air tweezers light. This version could be an add on, after market pickup and placement tool for use with any LED based curing wand currently sold. Two versions could be made, one with an internal source of vacuum, forming a cordless vacuum source most likely used with cordless curing wands, and the other being connected by tubing to a high volume vacuum source found in almost all dental offices for use with a corded curing wand.

Device 50 could also be made without an internal vacuum source, but still provide full curing and vacuum operation by connecting the device by tubing to a remote vacuum source, thus forming air tweezers corded.

An advantage of connecting device 50 to an external source of vacuum is that it saves the cost of a vacuum pump in the device 50, thereby allowing the sales price to be lowered. A disadvantage is that the effectiveness of the device 50 depends upon a constant vacuum from the in house vacuum system. A large fluctuation in the vacuum could cause the dental appliance to be dropped.

Figure 10A:
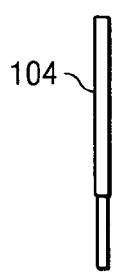
FIGS. 10a and 10b illustrate the flapper.
Figure 10B:
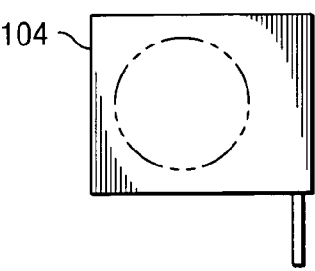
Figure 11:
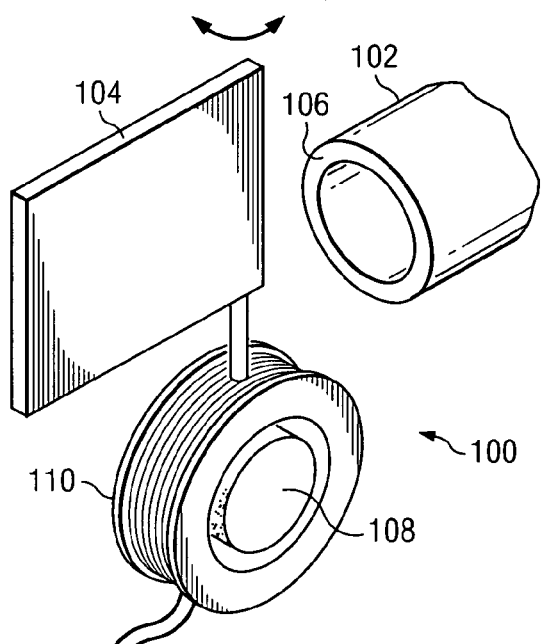
FIG. 11 illustrates a magnetic servo actuator.
Figure 13:
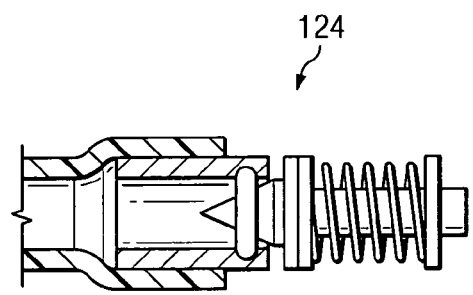
FIG. 13 illustrates a solenoid needle valve for the corded air tweezers.
Figure 12:
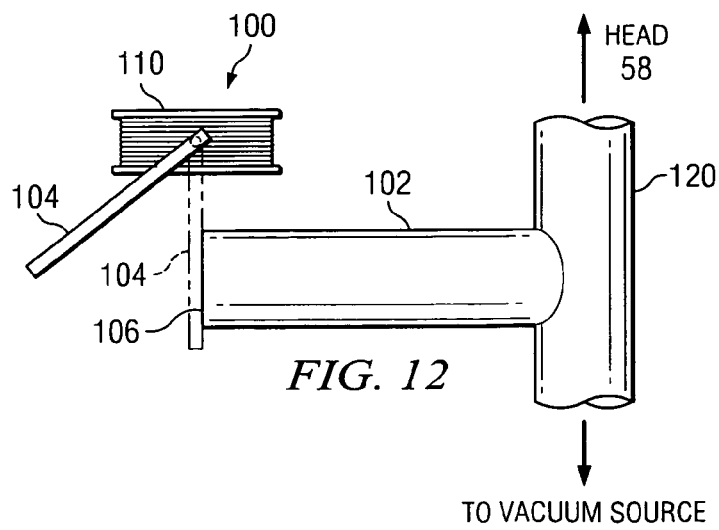
FIG. 12 is a top view of the magnetic servo actuator.

When a corded air tweezer model is used, it will need several additional components to interact with the remote vacuum source. A mechanism is needed to selectively isolate the head 58 and tunnel 88 from the vacuum source. One possible mechanism is a magnetic servo activator 100 mounted in device 50 and shown in FIGS. 11 and 12. Silicon tubing 120 connects the vacuum source to the head 58 as seen in FIG. 12. Tubing 120 forms a T with an open ended arm 102 of the T. Vacuum is always present in the portion of the tube below the T as seen in FIG. 12. A Flapper 104 is pivoted onto the activator 100 and can pivot about 90 degrees from an open position parallel the length of the tubing 102 as seen in FIGS. 10a and 11, opening the tube end 106 to bleed atmospheric pressure into the tubing 102 and preventing a vacuum from traveling to the head 58, to a closed position (FIG. 12 in broken line and FIG. 10b) with the flapper covering the end 106 of tubing 102 to allow vacuum to pass to the head 58 from the vacuum source. The flapper 104 is connected to a permanent magnet 108 pivotally mounted inside a wire coil 110. Supplying electrical current to the wire coil will rotate the magnet 108 and flapper into one position against the force of a return spring (not shown), while removing current to the wire coil will cause the magnet 108 and flapper 104 to move to the other position under the influence of the return spring. Thus, the vacuum can be applied and removed simply by supplying current to the coil 110 or not, depending on the state desired. Flapper 104 can be 6 mm by 5 mm, for example. FIG. 13 illustrates an alternative mechanism to select vacuum and illustrates a solenoid needle valve 124 that would be mounted within the corded air tweezers in the vacuum circuit that would open to allow vacuum to the head 58 when electric current is supplied to the solenoid in valve 124 and close to block vacuum in the absence of electric current.

All of the above described variations of device 50, air tweezers freedom, air tweezers light and air tweezers corded, still have the advantage of using the identical collimator 76.

While several embodiments of the invention have been illustrated in the accompanying drawings and described in the foregoing Detailed Description, it will be understood that the invention is not limited to the embodiments disclosed, but is capable of numerous rearrangements, modifications and substitutions of parts and elements without departing from the spirit and scope of the invention.

The invention claimed is:

1. An apparatus, comprising:
   a handle;
   a extension extending from a first end of the handle;
   a dental appliance pickup device mounted on the extension, the pickup device defining a cavity;
   a source of vacuum to define a relative vacuum in said cavity to capture a dental appliance with said pickup device to facilitate positioning the dental appliance;
   a light source positioned on the extension to tack the dental appliance in position; and
   a control mechanism to prevent the light source from being activated when the source of vacuum is activated.

2. The apparatus of claim 1 wherein the dental appliance pickup device includes a flexible, disposable skirt.

3. The apparatus of claim 1 wherein the light source emits light rays and the light rays from the light source pass through the cavity.

4. The apparatus of claim 1 further capable of curing an adhesive securing the dental appliance.

5. The apparatus of claim 1 further having a source of drying air.

6. The apparatus of claim 1 further having a disposable collimator.

7. The apparatus of claim 2 having multiple light sources at different wavelengths.

8. The apparatus of claim 1 further having two switches that must be closed simultaneously to activate the light source.

9. The apparatus of claim 6 wherein the collimator is acrylic and has a hyperbolic funnel shape, the exterior of the funnel having an opaque coating, light from the light source exiting an end of the collimator.

10. The apparatus of claim 9 further having a flexible disc at the end of the collimator.

11. The apparatus of claim 6 further having an O-ring between the collimator and the extension to maintain vacuum to the collimator, the collimator having a tunnel to convey the vacuum to an end of the collimator.

12. The apparatus of claim 2 wherein the light source is a beam of 1 to 2 degree arc passing through the skirt, the light source being concentric with the skirt.

13. The apparatus of claim 1 wherein the control mechanism includes a vacuum switch to activate the vacuum source and a slide switch to activate the light source, the slide switch being prevented from activating the light source when the vacuum switch activates the vacuum source.

14. An apparatus, comprising:
   a handle;
   an extension extending from a first end of the handle;
   a light source positioned on the extension to tack a dental appliance or cure an adhesive securing the dental appliance in position, the light source having at least one first light source having a first wavelength and at least one second light source having a second wavelength;
   a lens, the light from said light source passing through the lens;
   a disposable collimator removably attached to the extension, wherein the collimator is acrylic and has a hyperbolic funnel shape exterior and an interior hollow vacuum tunnel, the exterior of the funnel having an opaque coating, light from the light source passing through the collimator and exiting an end of the collimator when the collimator is attached to the extension, a flexible disc at the end of the collimator;
   a source of vacuum to define a relative vacuum in said vacuum tunnel to capture a dental appliance with said flexible disc to facilitate positioning the dental appliance, an O-ring positioned between the collimator and the extension to maintain vacuum in the tunnel when the collimator is attached to the extension; and
   wherein use of the light from the light source with the collimator attached to the extension tacks a dental appliance and use of the light from the light source with the collimator removed cures the adhesive.

15. The apparatus of claim 14 further having two switches that must be closed simultaneously to activate the light source.

16. The apparatus of claim 14 wherein the first light source is a blue LED and the second light source is a UV LED.

17. The apparatus of claim 14 wherein the lens is convex except for a Fresnel portion over said second light source.

18. The apparatus of claim 14 further having a sensor to detect the attachment of the collimator to the extension, the apparatus preventing operation of the vacuum source when the collimator is not attached to the extension.

* * * * *